United States Patent [19]

Arakawa

[11] Patent Number: 4,651,202
[45] Date of Patent: Mar. 17, 1987

[54] VIDEO ENDOSCOPE SYSTEM

[75] Inventor: Satoshi Arakawa, Saitama, Japan

[73] Assignee: Fuji Photo Optical Co., Ltd., Saitama, Japan

[21] Appl. No.: 726,289

[22] Filed: Apr. 23, 1985

[30] Foreign Application Priority Data

May 16, 1984 [JP] Japan ................................ 59-70354[U]

[51] Int. Cl.$^4$ .............................................. H04N 7/18
[52] U.S. Cl. .......................................... 358/98; 128/4; 128/6
[58] Field of Search ........................... 358/98; 128/4, 6

[56] References Cited

U.S. PATENT DOCUMENTS 4,331,132  5/1982  Mukasa ..................................... 128/6

FOREIGN PATENT DOCUMENTS 0023077  3/1981  Japan ...................................... 358/98

Primary Examiner—James J. Groody
Assistant Examiner—John K. Peng
Attorney, Agent, or Firm—Young & Thompson

[57] ABSTRACT

A video endoscope system includes an endoscope having in its imaging system a solid state imaging device for generating a video signal of an image of an object to be observed or examined which in turn is transmitted through a control circuit to a CRT display to be visualized thereon as a television picture and to a video tape recorder. A manually operable control switch on a hand-held control section of the endoscope actuates the video tape recorder to start recording the transmitted video signal on a video tape when desired. The provision of the control switch operable remotely from the video recorder permits an endoscope operator to start the video recorder when desired, without calling on others observing the television picture to perform the recording operation, which avoids the risk of delays and faulty communications that might otherwise result.

5 Claims, 2 Drawing Figures

VIDEO ENDOSCOPE SYSTEM

FIELD OF THE INVENTION

The present invention relates to a video endoscope system, and more particularly to a video endoscope system for recording an image of an object to be observed or inspected as well as displaying it on a monitor.

BACKGROUND OF THE INVENTION

In order to observe, inspect and record an image of the inside of a cavity or opening of a living body or machinery, a fiberoptic endoscope was used heretofore of the type having in its imaging system an image transmitting fiber bundle for transmitting an image of the inside of an object. The image thus transmitted is observed through an eyepiece or photographed by a camera.

Thanks to recent progress in semiconductor technology, there have been developed video endoscopes of the type having in their imaging system a solid state imaging device, such as a charge-coupled device (CCD) and an MOS image sensor, which accepts an optical image of an object and converts it into electrical signals, which in turn are transmitted to a cathode-ray tube (CRT) display to be visualized thereon and/or recorded on a video tape. Such video endoscopes are described for example in Japanese Pat. Application No. 238971/1983, and Japanese Utility Model Application No. 194969/1983, and filed Dec. 20, 1983. Such video endoscope systems make possible the monitoring on a CRT of a television picture of an object by a number of persons or surgical operators simultaneously or the recordation of pictures of affected parts or the like, thereby to achieve a rapid and correct diagnosis.

However there has been in such video endoscope systems an operational difficulty, namely, that the operator of the video endoscope is usually remote from the CRT monitor and any recording equipment, each having an activation switch provided therein. This requires communication between the operator of the endoscope and the operator or operators of the CRT monitor, the recording equipment and the like; and in the event of less than optimum communication, it may take a long time to make an inspection, diagnosis or judgment and in some cases an erroneous diagnosis or misjudgment may result.

OBJECTS OF THE INVENTION

It is therefore an object of the present invention to provide a video endoscope system which eliminates the shortcomings discussed above.

It is another object of the present invention to provide a video endoscope system which enables the operators of a video endoscope to control at least a video tape recorder (VTR) while operating the video endoscope.

SUMMARY OF THE INVENTION

In accordance with the present invention, a video endoscope system comprises a video endoscope of the type having in its imaging system a solid state imaging device for converting an optical image formed thereon into electrical signals which in turn are transmitted as a video signal to a CRT monitor, a VTR and copy producing equipment through a central control unit (CCU), said video endoscope being provided on its control section with at least a control switch for the VTR.

The provision of the control switch on the control section of the video endoscope enables an operator who is controlling a video endoscope by monitoring on the CRT a picture from the video endoscope, to control the VTR without the need to communicate with his assistant or assistants, so that he can record a video signal on a video tape at any time he chooses to do so.

The provision of the control switch permits the operation of the VTR during various operations of the video endoscope.

In accordance with the present invention, a rapid and correct diagnosis is assured and a video signal recording and a copy of a picture of an affected part are timely made.

BRIEF DESCRIPTION OF THE DRAWINGS

Other objects and features of the present invention will become apparent from a consideration of the following detailed description with reference to the accompanying drawings, wherein.

DETAILED DESCRIPTION OF THE INVENTION

Figure 1:
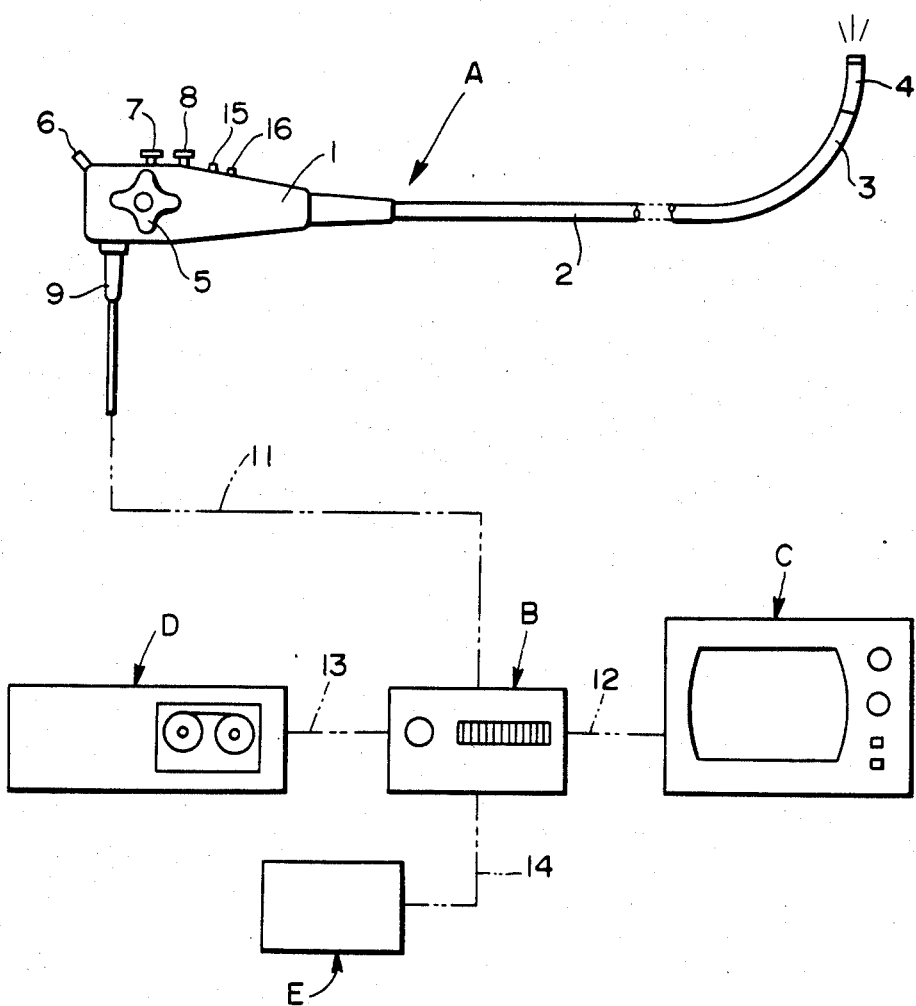
FIG. 1 schematically shows, partially in a block diagram, a video endoscope system of the present invention.

Referring now to FIG. 1, there is shown therein a video endoscope system comprising a video endoscope A of the type having in its imaging system a solid state imaging device, a central control unit (CCU) B, a monitor, such as a cathode-ray tube (CRT) display C, a video tape recorder (VTR) D and copy producing equipment E. These items are well known to those skilled in the art and so a further consideration of the construction thereof is omitted for simplicity. The video endoscope A comprises a hand-held operating section 1, a flexible insertable section 2 having a bend 3, a viewing head 4 including therein a solid state imaging device such as a charge coupled device (CCD), an MOS imaging sensor and its included driving and amplifying circuits and a connection section 9.

As is well known, the flexible section 2 includes therein a light guide means comprising, for example, an optical fiber bundle, pipes for air feed and water feed, a forceps guide channel, bending control wires, etc. The light guide means extending through the connection section 9 is positioned at the end face within a light source unit (not shown). The solid state imaging device is connected to the central control circuit B by means of cables 11 extending through the flexible section 2 and the connection section 9. The CRT display C, VTR D and copy producing equipment E are connected to the central control circuit B by means of cables 12, 13 and 14, respectively.

On the operating section 1 of the video endoscope A, there are provided manually operable start control buttons 15 and 16 as well as a control knob 5 for bending the bend 3 to a desired angle, a forceps channel opening 6, a water feed and air feed button 7 and a suction button 8.

Figure 2:
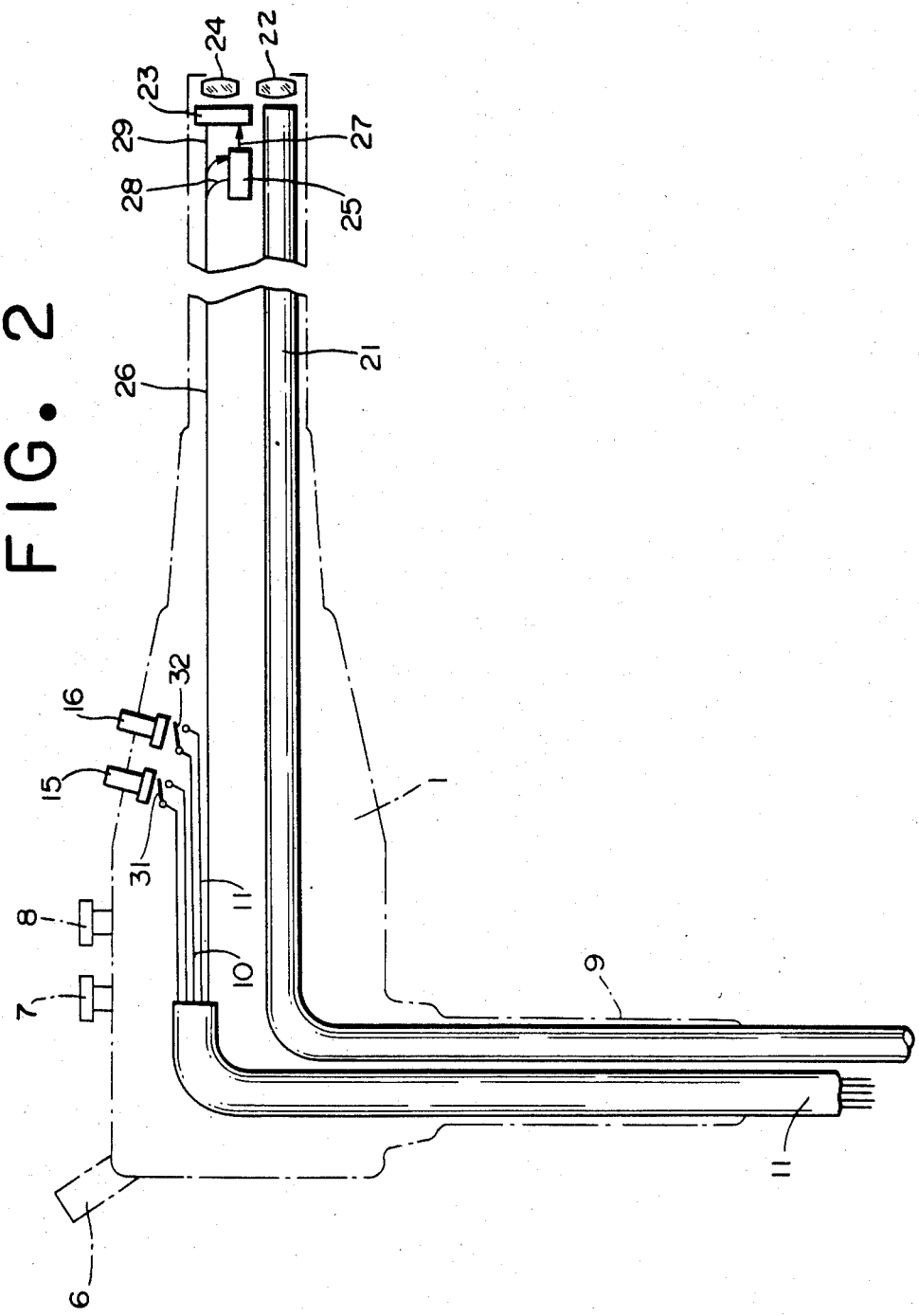
FIG. 2 schematically shows in cross section and in partly cutaway view the construction of a video endoscope included in the video endoscope system of FIG. 1.

Referring to FIG. 2 shown therein in schematic cross section is the video endoscope shown in FIG. 1 incorporating an imaging system. The imaging system comprises a light guide 21 for transmitting light therethrough to illuminate a desired region inside a cavity of a body (not shown) through a lens 22, a solid state imaging device 23 which is adapted to receive an image formed by an objective lens 24 and convert it to electrical signal, a driving circuit 25 for the solid state imaging device 23 and a cable 26 comprising plural leads for time serial signals from the solid state imaging device, vertical and horizontal synchronizing signals, clock signals and power supply. The driving circuit 25 which is supplies with clock signals from the central circuit B produces driving pulses shifted in phase relative to each other on input lead 27 to drive the solid state imaging device 23. The driving circuit 25 further generates vertical and horizontal synchronizing signals on output leads 28 which in turn are supplied to the central control circuit B. The solid state imaging device 23 thus driven produces in response to the clock signals video signals in timed sequence on lead 29 in a known manner which in turn are transmitted to the central control circuit B. Such an imaging system is disclosed in the Japanese patent application and Japanese utility model application referred to above.

The video endoscope A further has normally open start switches 31 and 32 on the operating section thereof. The start switches 31 and 32 are closed by pushing the control buttons 15 and 16 to record a video signal and produce a copy. Each of buttons 15 and 16 is effective to close its associated switch for as long as the button is manually depressed by the operator. It should be noted that the VTR D and copy producing equipment E may in addition by provided with switches, not shown, which can be operated by an assistant remote from an operator manipulating the endoscope. It is preferred to indicate on the CRT the direction and angle of turning of the knob 5. This indication of the direction and angle of turning gives useful information to the operator of the endoscope. Such apparatus is for example disclosed in detail in Japanese Utility Model application No. 198416/1983.

When using the video endoscope system in accordance with the present invention, the operator operates the endoscope A while monitoring a picture from the endoscope A and/or the indication of the direction and angle of turning of the knob 5 on the CRT display C so as to position the viewing head 4 so that it will be directed to a desired part of the inside of the cavity to be observed. During the operation, the operator of the endoscope A can actuate the VTR D or the copy producing equipment E by pushing the button 15 or 16 at any time when he feels he may wish to reexamine in detail the picture of that part of the inside of the cavity that is being shown on the CRT display C so as to make a record of the picture as a video signal on a video tape or by makeing a permanent copy of the picture. The operation can be effected while operating the control knob 5 without calling on his assistants for the actuation of the VTR D or the copy producing equipment E. On the other hand, it is of course possible for the assistants who are also observing pictures presented on the CRT display C to actuate the VTR D and/or the copy producing equipment E by operating the conventional switches provided thereon for recording the pictures on the video tape and/or making copies thereof as they choose.

As will be apparent from the foregoing, according to the present invention, a video endoscope system includes a video endoscope provided with push buttons for the actuation of a VTR and copy producing equipment, the push buttons enabling the operator of the video endoscope to actuate himself the VTR and copy producing equipment which are remote from the operator without calling on his assistants for the actuation of the VTR and copy producing equipment. Accordingly, a video endoscope system according to the invention makes it unnecessary to communicate with the assistants in any way that might divert their attention from pictures presented on the CRT display, with the result that there can be no problem of communication between the endoscope operator and his assistants, and rapid and accurate inspection or diagnosis can be made and correct judgment can be reached.

Although the present invention has been fully described by way of example with reference to the accompanying drawings, it is to be noted that various changes and modifications can be made, as will be apparent to those skilled in the art. Therefore, unless otherwise such changes and modifications depart from the scope of the present invention, they should be construed as included therein.

What is claimed is:

1. A video endoscope system comprising:
   an endoscope having a hand-held operating section and a viewing head in which a solid state imaging device is provided for generating video signals associated with an image of an object observed by the endoscope;
   positioning means disposed on said hand-held operating section for aligning said viewing head in any desired viewing direction;
   video display means for visibly displaying the image of the object;
   recording means for recording said video signals on a video signal recording medium, said recording means being remote from said hand-held operating section;
   copy producing means for producing a hard copy of the image of the object;
   a control circuit through which said video signals are transmitted to said video display means, recording means and copy producing means; and
   first means on said hand-held operating section for selectively enablng and disabling at least said recording means.

2. A video endoscope system as defined in claim 1, wherein said first means comprises two manually operable push buttons for actuating said recording means and copy producing means, respectively.

3. A video endoscope system as defined in claim 1, and manually operable actuating means on said recording means and copy producing means.

4. A video endoscope system as defined in claim 1, wherein said first means is a manually operable push button provided on the hand-held operating section.

5. A video endoscope system as defined in claim 4, wherein said manually operable push button operates to enable said recording means while said push button is depressed, and to disable said recording means when said push button is released.

* * * * *